(12) United States Patent
Li et al.

(10) Patent No.: US 9,322,796 B2
(45) Date of Patent: Apr. 26, 2016

(54) FLUID RESISTIVITY SENSOR

(75) Inventors: Jing Li, Houston, TX (US); Michael S. Bittar, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 120 days.

(21) Appl. No.: 13/695,368

(22) PCT Filed: Jun. 1, 2010

(86) PCT No.: PCT/US2010/036898
§ 371 (c)(1),
(2), (4) Date: Dec. 14, 2012

(87) PCT Pub. No.: WO2011/152820
PCT Pub. Date: Dec. 8, 2011

(65) Prior Publication Data
US 2013/0099808 A1    Apr. 25, 2013

(51) Int. Cl.
*G01N 27/06* (2006.01)
*G01N 27/07* (2006.01)
*G01V 3/24* (2006.01)
G01N 27/04 (2006.01)
G01N 27/02 (2006.01)

(52) U.S. Cl.
CPC ............ *G01N 27/06* (2013.01); *G01N 27/07* (2013.01); *G01V 3/24* (2013.01); *G01N 27/02* (2013.01); *G01N 27/04* (2013.01)

(58) Field of Classification Search
CPC ....... G01N 27/04; G01N 27/06; G01R 27/02; G01R 27/07
USPC .................................. 324/722, 719, 692, 693
See application file for complete search history.

(56) References Cited

U.S. PATENT DOCUMENTS

| | | | | |
|---|---|---|---|---|
| 3,305,771 A | | 2/1967 | Arps | |
| 3,404,335 A | | 10/1968 | Kidder | |
| 3,470,465 A | * | 9/1969 | Wuschke | 324/722 |
| 3,989,009 A | * | 11/1976 | Robar et al. | 119/14.08 |
| 4,536,714 A | * | 8/1985 | Clark | 324/338 |
| 4,786,874 A | | 11/1988 | Grosso et al. | |
| 4,860,581 A | * | 8/1989 | Zimmerman et al. | 73/152.26 |
| 5,235,285 A | * | 8/1993 | Clark et al. | 324/342 |
| 5,339,037 A | | 8/1994 | Bonner et al. | |
| 5,463,320 A | | 10/1995 | Bonner et al. | |

(Continued)

FOREIGN PATENT DOCUMENTS

WO    WO-2011152820 A1    12/2011

OTHER PUBLICATIONS

"International Application Serial No. PCT/US2010/036898, International Preliminary Report on Patentability mailed Dec. 13, 2012", 7 pgs.

(Continued)

*Primary Examiner* — Jermele M Hollington
*Assistant Examiner* — Christopher McAndrew
(74) *Attorney, Agent, or Firm* — Schwegman, Lundberg & Woessner, P.A.; Benjamin Fite

(57) ABSTRACT

Various embodiments include apparatus and methods of determining resistivity of fluids downhole in a well. The apparatus and methods may include using a sensor that employs a focused electric dipole as a transmitter and a uses a receiver to detect the electric current strength in the fluid under measurement responsive to the transmitter. Additional apparatus, systems, and methods are disclosed.

29 Claims, 8 Drawing Sheets

(56) References Cited

U.S. PATENT DOCUMENTS

| | | | |
|---|---|---|---|
| 5,959,455 A * | 9/1999 | Brown | 324/445 |
| 6,046,593 A | 4/2000 | Eisenmann et al. | |
| 6,100,696 A * | 8/2000 | Sinclair | 324/339 |
| 6,373,254 B1 | 4/2002 | Dion et al. | |
| 6,573,722 B2 * | 6/2003 | Rosthal et al. | 324/338 |
| 6,755,247 B2 | 6/2004 | Moake et al. | |
| 6,787,901 B2 * | 9/2004 | Reyes et al. | 257/724 |
| 6,801,039 B2 | 10/2004 | Fabris et al. | |
| 6,927,578 B2 | 8/2005 | Homan et al. | |
| 6,956,376 B2 | 10/2005 | Salamitou | |
| 6,958,610 B2 * | 10/2005 | Gianzero | 324/342 |
| 7,078,909 B2 | 7/2006 | Feng et al. | |
| 7,151,377 B2 | 12/2006 | Chouzenoux et al. | |
| 7,157,900 B2 | 1/2007 | Quackenbush et al. | |
| 7,227,363 B2 * | 6/2007 | Gianzero et al. | 324/342 |
| 7,256,582 B2 | 8/2007 | Gorek et al. | |
| 7,405,572 B2 | 7/2008 | Quackenbush et al. | |
| 7,436,184 B2 | 10/2008 | Moore | |
| 7,501,839 B2 * | 3/2009 | Chan et al. | 324/754.18 |
| 7,525,315 B2 | 4/2009 | Fredette et al. | |
| 7,714,451 B2 * | 5/2010 | Lee et al. | 257/786 |
| 7,927,898 B2 * | 4/2011 | Tosi et al. | 438/29 |
| 2003/0016020 A1 * | 1/2003 | Gianzero | 324/342 |
| 2003/0025639 A1 * | 2/2003 | Rodney et al. | 343/719 |
| 2005/0099184 A1 | 5/2005 | Gianzero et al. | |
| 2007/0018659 A1 * | 1/2007 | Homan et al. | 324/693 |
| 2008/0169817 A1 * | 7/2008 | Morrison et al. | 324/365 |
| 2009/0179648 A1 | 7/2009 | Fredette et al. | |
| 2009/0267619 A1 * | 10/2009 | Slezak et al. | 324/663 |
| 2009/0322338 A1 | 12/2009 | Godefroy et al. | |

OTHER PUBLICATIONS

"United Kingdom Application Serial No. 1222312.9, Office Action mailed Nov. 29, 2013", 2 pgs.

"United Kingdom Application Serial No. 1222312.9, Response filed Apr. 4, 2014 to Office Action mailed Nov. 29, 2013", 25 pgs.

"International Application Serial No. PCT/US10/36898, Search Report mailed Feb. 22, 2011", 5 pgs.

"International Application Serial No. PCT/US10/36898, Written Opinion mailed Feb. 22, 2011", 8 pgs.

Yongmin, Z., et al., "The Performance Evaluation of MWD Logging Tools Using Magnetic and Electric Dipoles by Numerical Simulations", IEEE Transactions on Geoscience and Remotesensing, IEEE Service Center, Piscataway NJ, US,vol. 34, No. 4 (Jul. 1, 1996), 6.

"Canadian Application Serial No. 2,800,469, Response filed Jan. 21, 2015 to Office Action mailed Jul. 28, 2014", 19 pgs.

"Canadian Application Serial No. 2,800,469, Office Action mailed Jul. 28, 2014", 3 pgs.

* cited by examiner

FLUID RESISTIVITY SENSOR

RELATED APPLICATIONS

This application is a U.S. National Stage Filing under 35 U.S.C. 371 from International Application No. PCT/US2010/036898, filed on Jun. 1, 2010, and published as WO 2011/152820 A1 on Dec. 8, 2011, which application and publication are incorporated herein by reference in their entirety.

TECHNICAL FIELD

The invention relates generally to systems having well logging capability.

BACKGROUND

In drilling wells for oil and gas exploration, understanding the structure and properties of the geological formation surrounding a borehole provides information to aid such exploration. However, the environment in which the drilling tools operate is at significant distances below the surface and measurements to manage operation of such equipment are made at these locations. Further, the usefulness of such measurements may be related to the precision or quality of the information derived from such measurements.

DETAILED DESCRIPTION

The following detailed description refers to the accompanying drawings that show, by way of illustration, various example embodiments of the invention. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description and accompanying drawings are, therefore, not to be taken in a limiting sense.

Figure 1:
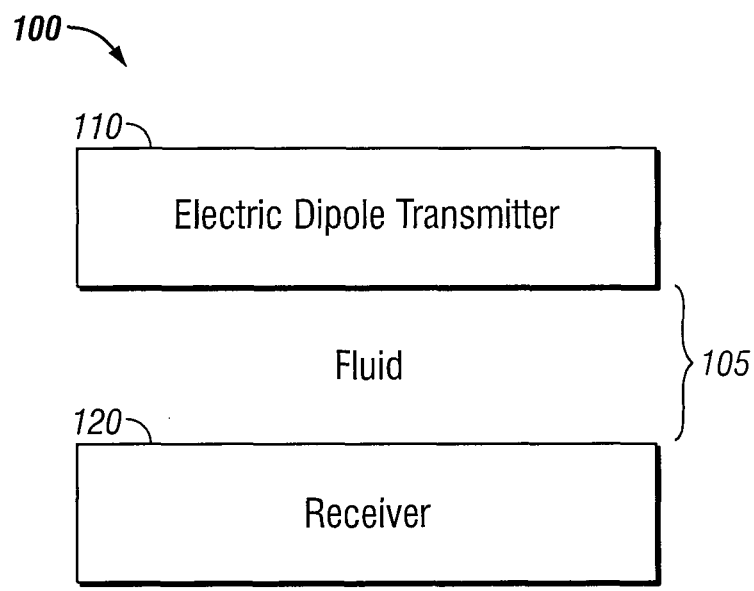
FIG. 1 shows a block diagram of an example of an apparatus including a sensor to measure conductivity of a fluid, according to various embodiments.

FIG. 1 shows a block diagram of an example of an apparatus 100 including a sensor 105 to measure conductivity of a fluid. Sensor 105 has an electric dipole transmitter 110 to induce an electric current in the fluid and a receiver 120 to detect electric current strength in the fluid in response to inducing the electric current. An electric dipole transmitter can be realized as instrumentality to apply a voltage across a gap. The gap may be an electrically insulated section separating two electrodes coupled to a voltage source. The applied voltage can be a low frequency voltage. For example, the applied voltage may be a 12 kHz signal with a 1 V amplitude. These values for an applied voltage are examples. Other frequencies and amplitudes may be used.

Electric dipole transmitter 110 can be structured as a focused electric dipole transmitter. The focused electric dipole can be employed to induce a longitudinally-polarized current in the fluid. The electric dipole transmitter can be realized by a pair of metal tubes. The metal tubes may have a rigid structure. Such tubes can have various shapes. The term "tube" refers to a structure that can contain fluid and/or allow flow of the fluid through the structure defining the tube. The tubes can be mounted on a drill collar or other structure coupled to the drill collar or on a cable wire or other structure coupled to the cable wire for use in drilling operations.

Receiver 120 can be realized as a toroid receiver to detect the current strength. A toroid receiver is constructed as a receiver having windings of wire, or equivalent structure, over a donut-shaped core material in which the measurement of a signal is electrodeless. Receiver 120 and transmitter 110 of sensor 105 can be arranged such that receiver 120 receives less direct interference from transmitter 110, as compared to existing a sensor using two toroids. Sensor 105 can be structured for an implementation in the borehole of a well as a measurements-while-drilling (MWD) system such as a logging-while-drilling (LWD) system or as a wireline system. The housing containing sensor device 105 can include flow control components, such as a pump, to control collection of the fluid within sensor 105 for measurement of the conductivity of the fluid.

Early resistivity sensors included several electrodes that are used to inject currents into a fluid and to detect the voltage drop over certain distance. This could be accomplished using four electrodes in the form of short metal tubes separated by short insulating tubes. However, to protect the circuitry compartment under high fluid pressure condition, such electrodes should be well sealed. Using seals, such as eight seals with four electrodes, which adds additional components, may reduce the sensor's reliability under high pressure condition.

Another approach to measure fluid conductivity has utilized two insulating tubes, each of which is provided with both transmitter toroid and receiver toroid. The two transmitter toroids are oppositely poled so that the current induced in two tubes tends to form a complete circulation loop. Since two tubes and two sets of toroid transmitters and receivers are employed, the sensor size is made relatively large.

Another design used only two toroids, one as a transmitter and the other as a receiver, installed on a straight tube. The straight tube was composed of two sections of metal tube separated by a short insulation tube. This design has less driving power compared with the above two transmitter toroid design. In addition, this design does not have a configuration that forms a closed current loop in the fluid provided by the above two transmitter toroid design. Due to these differences with respect to the two transmitter toroid design, two sections of metal tubes are used to guide the current flow to provide measurable signal strength.

In the above conventional two toroid-based sensor designs, the transmitter toroid and the receiver toroid are co-axial and their field polarizations are parallel to each other. Such a structure may inevitably introduce direct coupling from the transmitter to the receiver, which generates interference to the received signal and reduces the sensitivity of the sensor.

Figure 2:
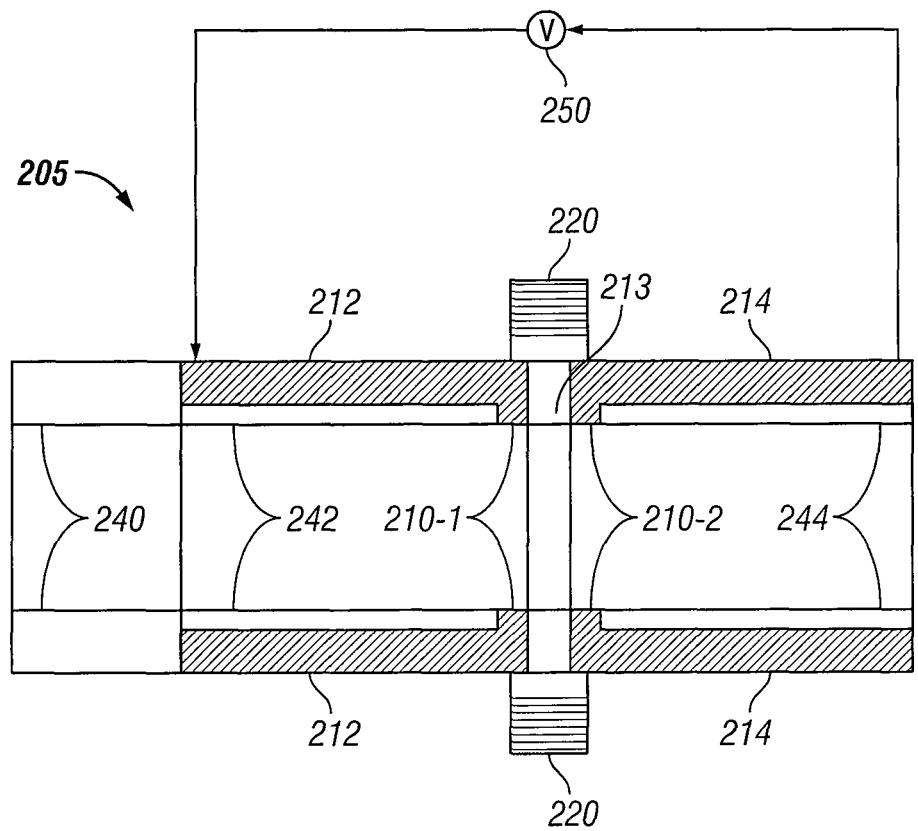
FIG. 2 illustrates an example of a sensor to measure conductivity of a fluid, according to various embodiments.

FIG. 2 illustrates an example of an apparatus including a sensor 205 to measure conductivity of a fluid, according to various embodiments of the invention. Sensor 205 includes two short ridged metal tubes 212 and 214 with ridged electrodes 210-1 and 210-2, respectively, that are separated by a short insulting tube 213 in the middle. Insulting tube 213 forms an insulating gap. The ridges and the insulating gap between them form a focused electric dipole. The gap can be small, such as less than an inch. For example, the gap length may be in the range of about 0.10 inches to about 0.25 inches. Other gap lengths may be used, including gap lengths greater than 1 inch. Insulating regions 242 and 244 can be used to provide the short ridge structure of metal tubes 212 and 214, respectively. Electrodes other than rigid electrodes may be used as electrodes 210-1 and 210-2.

As shown in FIG. 2, electrodes 210-1 and 210-2 effectively are tapered electrodes from the bodies of metal tubes 212 and 214. The shape of tapered electrodes 210-1 and 210-2 can be realized in a variety of shapes. For example, tapered electrodes 210-1 and 210-2 may be broad but short as shown in FIG. 2. Alternatively, tapered electrodes 210-1 and 210-2 can be short extending from the bodies of metal tubes 212 and 214 to a point-like end or termination, forming a spike-like structure. The shape can be selected to enhance operation as a focused electric dipole transmitter. Such tapered electrodes may be realized in the various embodiments, or similar embodiments, of sensors to measure conductivity of a fluid as discussed herein.

An insulating tube 240, at the left side as shown in FIG. 2, can be used to prevent short circulating the signal source and to enhance the current through the electric dipole. The focused electric dipole induces a relatively strong electric current in the tube's longitudinal direction across the insulating gap. The secondary magnetic field induced by this current is proportional to the fluid conductivity and is detected by toroid receiver 220. The focused electric dipole can be activated by voltage source 250. Voltage source 250 may be integrated with sensor 205 or separate from sensor 205 coupled by conductive leads to sensor 205.

Sensor 205 uses less seals for operation in high pressure conditions as compared to existing electrode sensors, which can provide enhanced reliability of sensor 205 relative to conventional sensors. Sensor 205 also avoids the use of a toroid transmitter, which can reduce direct coupling from the transmitter to the receiver. The reduced coupling may provide a received signal that is cleaner and easier to process.

Figure 3:
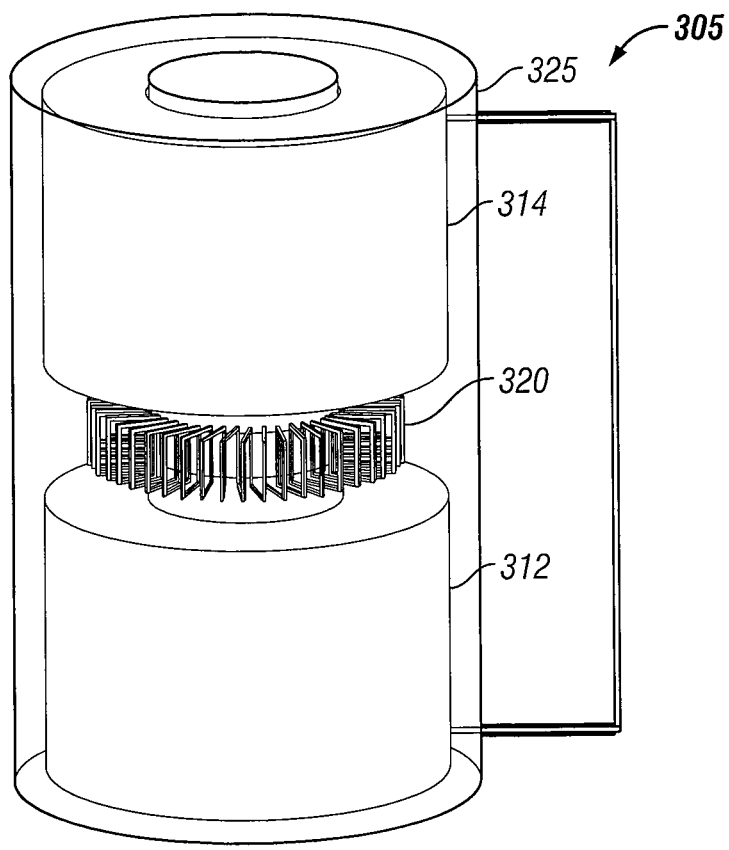
FIG. 3 illustrates an example of a rigid electric dipole sealed by epoxy, according to various embodiments.

FIG. 3 illustrates an example of an embodiment of a rigid electric dipole sealed by epoxy 325. Epoxy 325 provides a protective covering around metal tubes 312 and 314, insulating region 313, and toroid 320 forming sensor 305.

Figure 4:
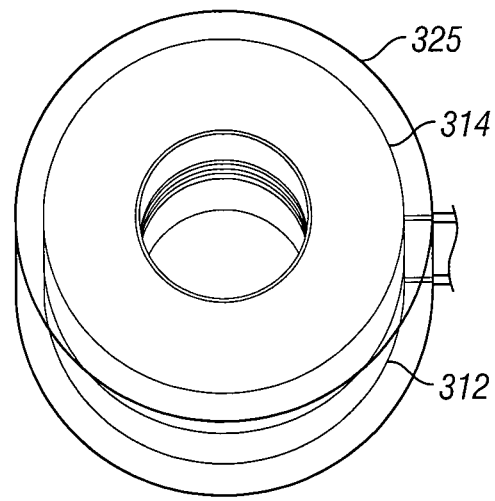
FIG. 4 illustrates a top view of the example electric dipole shown in FIG. 3, according to various embodiments.

FIG. 4 illustrates a top view of the example electric dipole shown in FIG. 3. Fluid to be measured is introduced into the opening of the tubes forming the rigid electric dipole.

Figure 5:
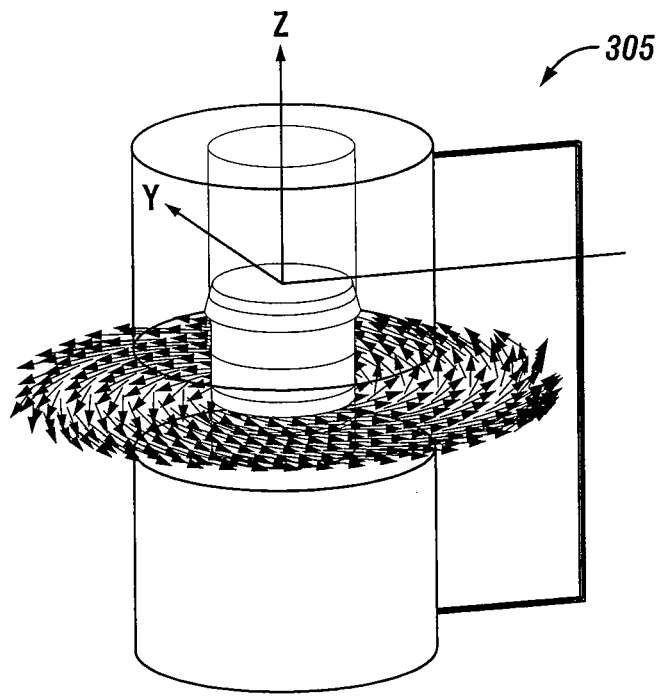
FIG. 5 illustrates a field pattern within the example sensor shown in FIG. 3, according to various embodiments.
Figure 6:
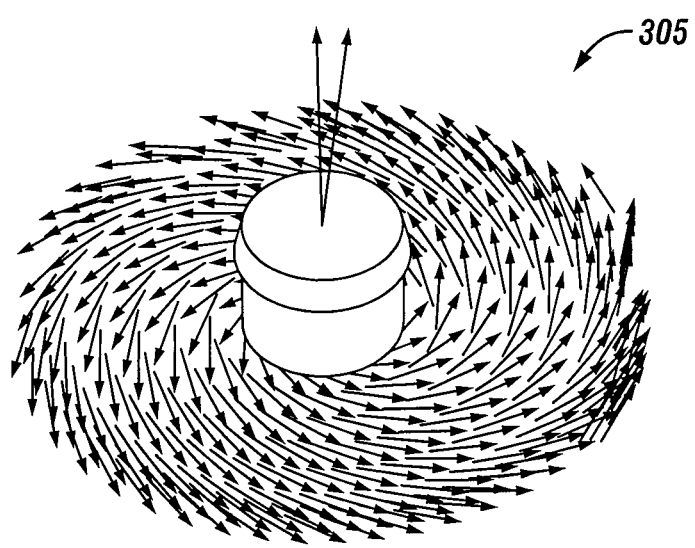
FIG. 6 illustrates focused-dipole-induced current and its secondary magnetic field within the example sensor shown in FIG. 3, according to various embodiments.

FIG. 5 illustrates a field pattern within the example sensor 305 shown in FIG. 3. The magnetic field is detected by toroid 320, shown in FIG. 3, from current induced in fluid in the opening of the tubes by an electric dipole transmitter. The focused-dipole-induced current and its secondary magnetic field within example sensor 305 are further illustrated in FIG. 6.

Figure 7:
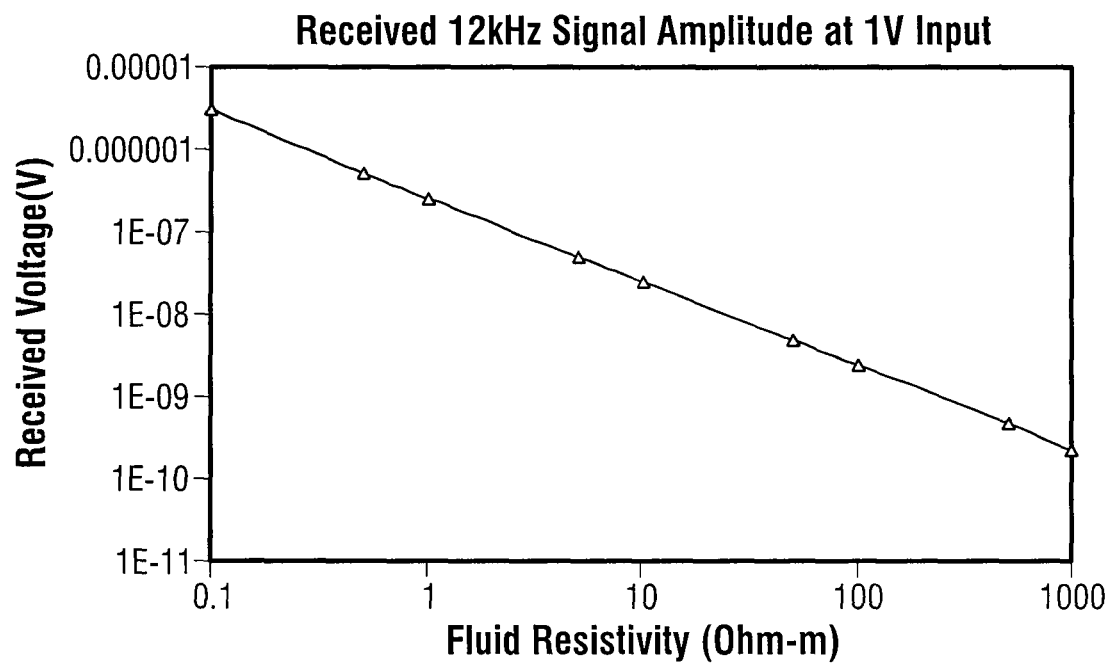
FIG. 7 shows received voltage versus fluid resistivity using an example sensor similar to that of FIG. 3, according to various embodiments.

FIG. 7 shows received voltage versus fluid resistivity using an example sensor similar to that of FIG. 3. As shown in FIG. 7, the focused electric dipole induces longitudinally-oriented electric current in the fluid contained in the tubes of the sensor. The current-induced magnetic field is unperturbed, not suffering interference from the transmitter. This lack of interference leads to a relatively high signal-to-noise ratio of the measurement and enhances the sensor's sensitivity.

Figure 8:
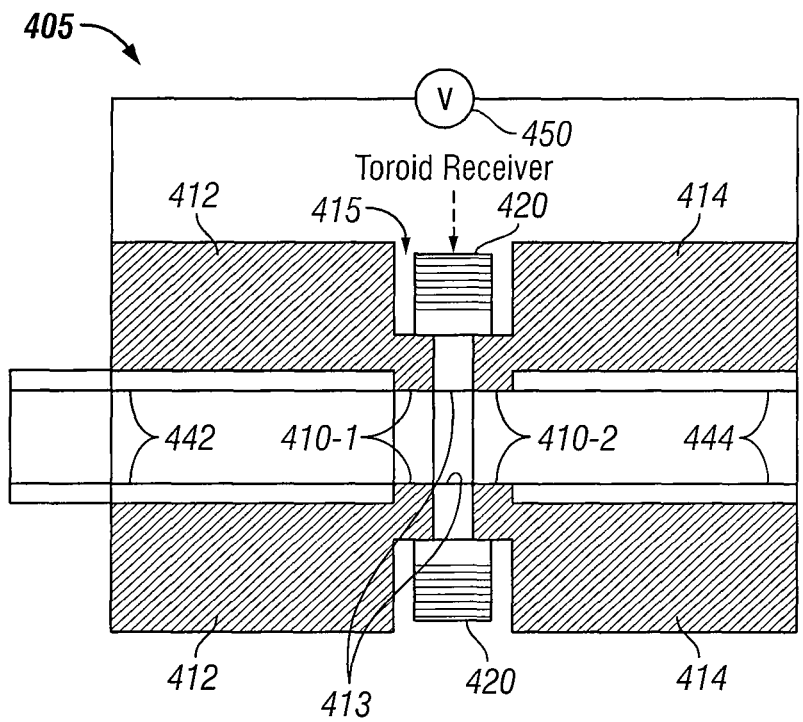
FIG. 8 shows an example of a sensor having a metal tube with a thicker wall, according to various embodiments.

FIG. 8 shows an example of a sensor 405 having a metal tube with a thicker wall than that of sensor 205 of FIG. 2. Sensor 405 includes two short ridged metal tubes 412 and 414 with ridged electrodes 410-1 and 410-2, respectively, that are separated by a short insulting tube 413 in the middle. The ridges and the insulating gap between them form a focused electric dipole. The focused electric dipole can be activated by voltage source 450. Voltage source 450 may be integrated with sensor 405 or separate from sensor 405 coupled by conductive leads. Insulating regions 442 and 444 can be used to provide the short ridge structure of metal tubes 412 and 414, respectively.

The wall of metal tubes 412 and 414 can be made thicker to form a groove 415 partially wrapping the toroid receiver 420, so that the secondary magnetic field can be further enhanced around receiver 420. In an embodiment, toroid 420 can be disposed effectively within the outer surface of metal tubes 412 and 414. As shown in FIG. 8, an example sensor 405 can have an insulating tube 413 with a center and toroid 420 with an outer surface at a radial distance from the center of insulating tube 413 such that the radial distance for toroid 420 is less than or equal to an effective radial distance of an outer surface of the metal tubes 412, 414 relative to the center of insulating tube 413. The wall thickness of metal tubes 412, 414 can be varied depending on the application. Groove 415 also provides protection and an installation frame to toroid 420.

Figure 9A:
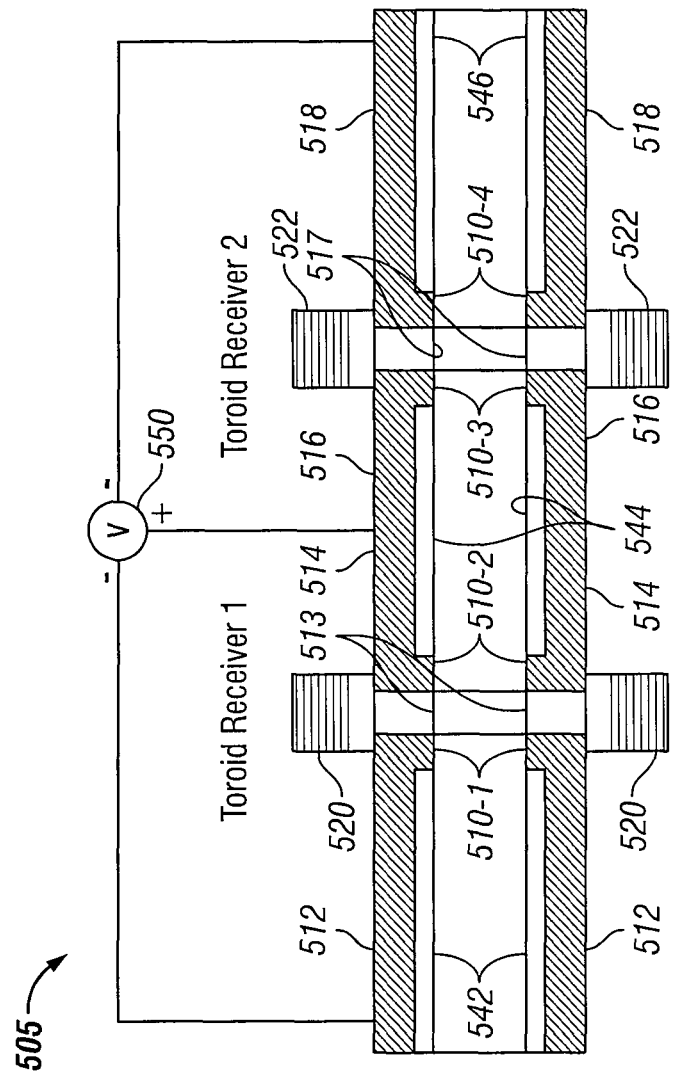
FIG. 9A shows an example of a sensor having dual receivers, according to various embodiments.

FIG. 9A shows an example of an embodiment of a sensor 505 having dual receivers 520 and 525. Sensor 505 includes two electric dipole transmitters. Sensor 505 includes two short ridged metal tubes 512 and 514 with ridged electrodes 510-1 and 510-2, respectively, that are separated by a short insulting tube 513 separating metal tubes 512 and 514 from each other. Sensor 505 also includes two short ridged metal tubes 516 and 518 with ridged electrodes 510-3 and 510-4, respectively, that are separated by a short insulting tube 517 separating metal tubes 516 and 518 from each other. As seen in FIG. 9, metal tubes 514 and 516 can be the same tube. The ridges and the insulating gap between them of each electric dipole transmitter form a focused electric dipole. The focused electric dipole transmitters can be activated by voltage source 550. Voltage source 550 may be integrated with sensor 505 or separate from sensor 505 coupled by conductive leads. Insulating regions 542 and 544 can be used to provide the short ridge structure of metal tubes 512 and 514, respectively, and Insulating regions 544 and 546 can be used to provide the short ridge structure of metal tubes 516 and 518, respectively.

Dual receivers 520 and 525 can be toroid receivers. The two toroidal receivers 520 and 522 can be installed to increase the sensor efficiency, though this may increase sensor size. With the two toroids oppositely wound, their output channels can be combined to increase signal-to-noise ratio.

Figure 9B:
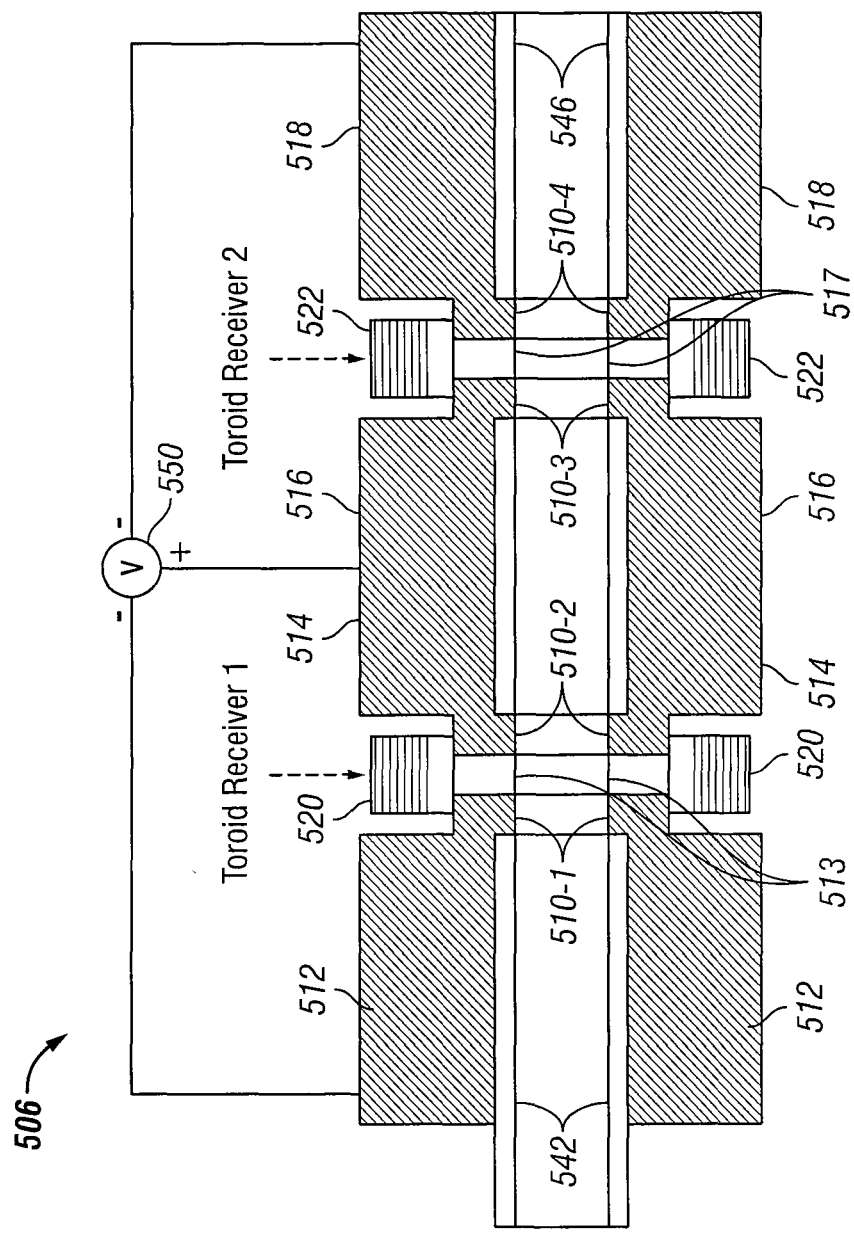
FIG. 9B shows the example of a sensor having dual receivers of FIG. 9A with thicker walls, according to various embodiments.

In various embodiments, the two toroid receiver arrangement of FIG. 9A can be structured with thicker walls such that one or both of toroid receivers 520, 522 are disposed in a groove similar in manner to the arrangement shown in FIG. 8. FIG. 9B shows an example sensor 506 structured as sensor 505 having dual receivers of FIG. 9A with thicker walls. A sensor to measure conductivity of a fluid can also be structured with more than two toroid receivers and more than two electric dipole transmitters. The number of toroid receivers can equal the number of electric dipole transmitters. The number of electric dipole transmitters can equal the number of pairs of metal tubes separated from each other by an insulating tube.

A design using a focused electric dipole transmitter with a toroid receiver avoids the direct coupling between the transmitter and receiver that can be found in existing toroidal sensors. A focused electric dipole transmitter provides a clean signal to the receiver. Simulated results show that the received signal amplitudes (both the real and imaginary parts) are only correlated to the fluid resistivity and the source output voltage, which significantly facilitates the electric circuitry design of the sensor. In addition, this design uses less seals compared to existing electrode sensors and has the capability to achieve a better reliability.

Figure 10:
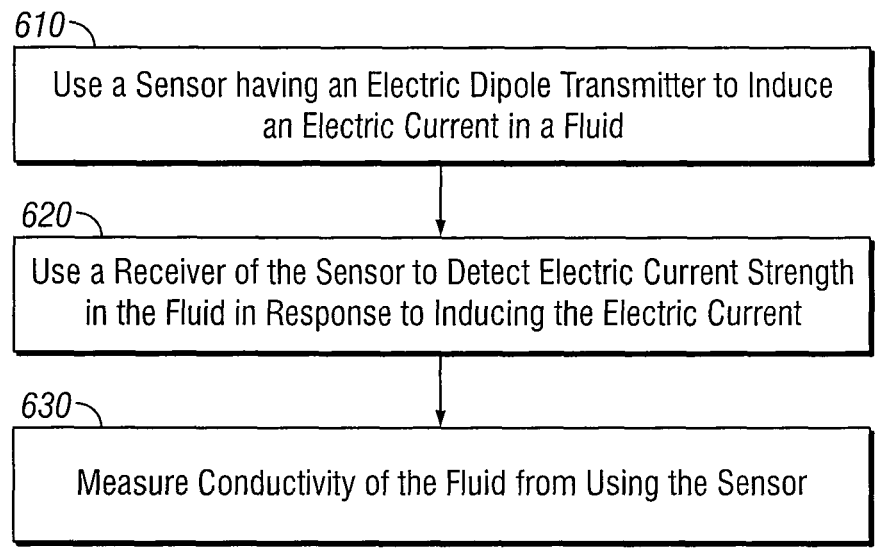
FIG. 10 shows features of an embodiment of a method that includes measuring conductivity of a fluid, according to various embodiments.

FIG. 10 shows features of an embodiment of a method that includes measuring conductivity of a fluid using a sensor having an electric dipole transmitter to induce an electric current in the fluid and having a receiver to detect electric current strength in the fluid in response to inducing the electric current. At 610, a sensor having an electric dipole transmitter is used to induce an electric current in a fluid. The electric dipole transmitter can be activated by applying a potential difference between a pair of metal tubes, where the metal tubes are separated from each other by an insulating tube. The fluid under measurement is contained in or is flowing through or within the metal tubes and the insulating tube. In another embodiment, the electric dipole transmitter can be activated by applying potential differences between two pairs of metal tubes. The activation can include applying a first potential difference between a first pair of the two pairs, where the metal tubes of the first pair are separated by a first insulating tube, and applying a second potential difference between a second pair of the two pairs, where the metal tubes of the second pair are separated by a second insulating tube. The fluid being is contained within or flowing through the first and second pairs and within or flowing through the first and second insulating tubes. Potential differences can be applied between two pairs of metal tubes with one of the metal tubes of the first pair being one of the metal tubes of the second pair. In other embodiments, more than two pairs of metal tubes may be used to induce electric current in a fluid in the tubes.

At 620, a receiver of the sensor is used to detect electric current strength in the fluid in response to inducing the electric current. When the electric dipole transmitter used to induce an electric current in the fluid is structured with one pair of metal tubes separated by an insulating tube, a single toroid can be used to receive a signal in response to the inducement of the electric current. The toroid receiver can be disposed around the insulating tube. When the electric dipole transmitter used to induce an electric current in the fluid is structured with two pairs of metal tubes, each of the two pairs separated by an insulating tube, two toroids can be used to receive signals in response to the inducement of the electric current. The first toroid receiver can be disposed around the insulating tube separating the metal tubes of one pair. The second toroid receiver can be disposed around the insulating tube separating the metal tubes of the other pair.

At 630, conductivity of the fluid is measured from using the sensor. Use of the sensor can be based on a selected signal-to-noise ratio for operation of the sensor. In a sensor arrangement having a multiple number of pairs of metal tubes, the sensor or a device coupled to the sensor can include a combiner coupled to an output channel from each of toroid receivers. The number of toroid receivers used can equal the number of pairs of metal tubes used. The combiner can be arranged relative to the output channels based on a selected signal-to-noise ratio for operation of the sensor.

In various embodiments, a sensor to measure conductivity of a fluid can be formed as a relatively simple structure capability of obtaining high reliability and sensitivity. The method of forming the sensor can include disposing an electric dipole transmitter unit to induce an electric current in the fluid and disposing a receiver unit relative to the electric dipole transmitter unit to detect electric current strength in the fluid in response to inducing the electric current. The sensor can be formed for applications downhole in a well.

The electric dipole transmitter unit can be structured by disposing a pair of metal tubes with the metal tubes separated from each other by an insulating tube, such that flow of the fluid to be measured can be directed through the metal tubes and the insulating tube. The receiver unit of the sensor can be structured by disposing a toroid around the insulating tube that separates the metal tubes. Alternatively, the electric dipole transmitter unit can be structured by disposing two pairs of metal tubes such that the metal tubes of one of the pairs are separated from each other by a first insulating tube and the metal tubes of the other pair are separated from each other by a second insulating tube such that the fluid can be directed into the metal tubes of the two pairs and into the first and second insulating tubes. The receiver unit of the sensor can be structured by disposing a first toroid around the first insulating tube and a second toroid around the second insulating tube.

In an embodiment, the electric dipole transmitter unit can be structured by disposing each of a pair of metal tubes with a thickness and with a groove adjacent an insulating tube, which separates the metal tubes from each other, such that a toroid receiver is disposed within a groove structure formed by the insulating tube and the grooves of the metal tubes. Alternatively, the electric dipole transmitter unit can be structured by disposing each of two pairs of metal tubes with a thickness and with a groove adjacent an associated insulating tube, which separates the metal tubes of the associated pair from each other, such that a first toroid receiver is disposed within a groove structure formed by one insulating tube and the grooves of its associated metal tubes and a second toroid receiver is disposed within a groove structure formed by another insulating tube and the grooves of its associated metal tubes.

In various embodiments, a sensor has disclosed herein has a simpler structure compared to existing sensors. The simpler structure can use a focused electric dipole source to effectively induce an electric current in the fluid that is free of transmitter interference and can be easily measured by toroid receivers. This design can provide the capability of obtaining high reliability and sensitivity.

Figure 11:
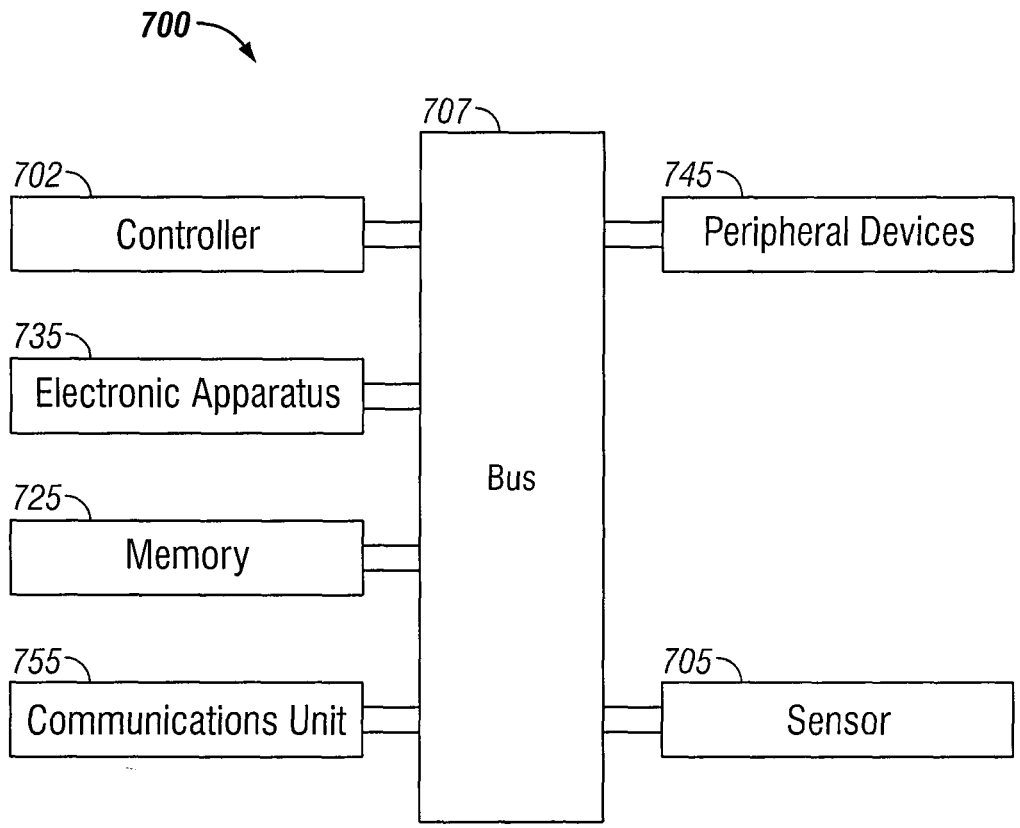
FIG. 11 depicts a block diagram of features of an embodiment of a system having one or more sensors to measure fluid conductivity, according to various embodiments.

FIG. 11 depicts a block diagram of features of an embodiment of a system 700 having a sensor 705. Sensor 705 can be realized as a sensor to measure conductivity in a fluid. Sensor 705 can be made robust to measure the fluid downhole in a well or at a surface with the fluid pumped under pressure to the surface. Sensor 705 can be structured and fabricated in accordance with various embodiments as taught herein.

System 700 can also include a controller 702, a memory 725, an electronic apparatus 735, and a communications unit 755. Various combinations of controller 702, memory 725, and communications unit 755 can be arranged to operate as a processing unit for sensor 705. Such a processing unit can process a signal from the sensor. The signal can be converted from a representation of a magnetic field to a conductivity of the fluid and/or from a representation of a measured electrical resistance of the fluid to conductivity of the fluid. Portions or all of controller 702, memory 725, and communications unit 755 can be structured to operate located downhole. Communications unit 755 can include downhole communications in a drilling operation. Such downhole communications can include a telemetry system. Communications unit 755 may be coupled to a communication line to provide measurement results to the surface of a well when sensor 705 is downhole in the well.

System 700 can also include a bus 707, where bus 707 provides electrical conductivity among the components of system 700. Bus 707 can include an address bus, a data bus, and a control bus, each independently configured. Bus 707 can also use common conductive lines for providing one or more of address, data, or control, the use of which is regulated by controller 702. Bus 707 can be configured such that the components of system 700 are distributed. Such distribution can be arranged between downhole components such as one or more sensors 705 and surface components such as a processing unit arranged as one or more components of system 700. Alternatively, the components can be co-located such as on one or more collars of a drill string or on a wireline structure.

In various embodiments, peripheral devices 745 include displays, additional storage memory, and/or other control devices that may operate in conjunction with controller 702 and/or memory 725. In an embodiment, controller 702 is a processor. A peripheral device arranged as a display can be used with instructions stored in memory 725 to implement a user interface to manage the operation of a sensor 705 in system 700 and/or components distributed within system 700.

Figure 12:
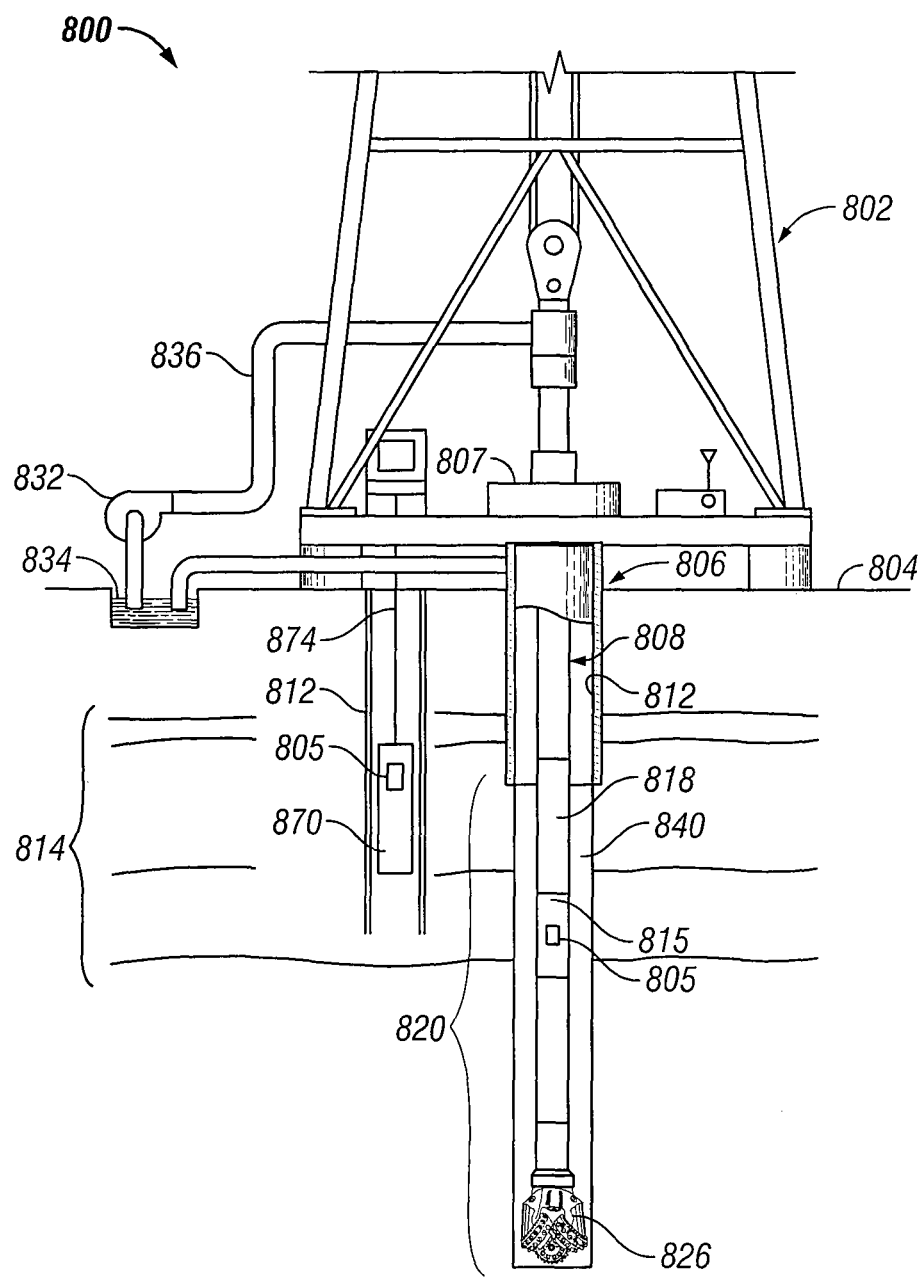
FIG. 12 depicts an embodiment of a system at a drilling site, according to various embodiments.

FIG. 12 depicts an embodiment of a system 800 at a drilling site, where system 800 includes a sensor 805 and electronics to determine conductivity of a fluid in a well. Sensor 805 can include an electric dipole transmitter to induce an electric current in the fluid and a receiver to detect electric current strength in the fluid in response to inducing the electric current. The electric dipole transmitter can be structured as a focused electric dipole transmitter. The receiver can be realized using a toroid receiver. Sensor 805 can be structured and fabricated in accordance with various embodiments as taught herein.

System 800 can include a drilling rig 802 located at a surface 804 of a well 806 and a string of drill pipes, that is, drill string 808, connected together so as to form a drilling string that is lowered through a rotary table 807 into a wellbore or borehole 812. The drilling rig 802 can provide support for drill string 808. The drill string 808 can operate to penetrate rotary table 807 for drilling a borehole 812 through subsurface formations 814. The drill string 808 can include drill pipe 818 and a bottom hole assembly 820 located at the lower portion of the drill pipe 818.

The bottom hole assembly 820 can include drill collar 815, sensor 805 attached to drill collar 815, and a drill bit 826. The drill bit 826 can operate to create a borehole 812 by penetrating the surface 804 and subsurface formations 814. Sensor 805 can be structured for an implementation in the borehole of a well as a measurements-while-drilling (MWD) system such as a logging-while-drilling (LWD) system. The housing containing sensor 805 can include flow control components, such as a pump, to control collection of the fluid within sensor 805 for measurement of the conductivity of the fluid. The housing containing sensor 805 can include electronics to activate sensor 805 and collect responses from sensor 805. Such electronics can include a processing unit to analysis signals sensed by sensor 805 and provide measurement results to the surface over standard communication mechanism for operating a well. Alternatively, electronics can include a communications interface to provide signals sensed by sensor 805 to the surface over standard communication mechanism for operating a well, where these sensed signals are analyzed at a processing unit at the surface. In another technique, the fluid can be pumped to the surface for measurement of the conductivity of the fluid. Various combinations of these techniques for generating measured conductivity of the fluid can be implemented.

In various embodiments, sensor 805 may be included in a tool body 870 coupled to a logging cable 874 such as, for example, for wireline applications. Tool body 870 housing sensor 805 can include flow control components, such as a pump, to control collection of fluid within sensor 805 for measurement of the conductivity of the fluid. Tool body 870 containing sensor 805 can include electronics to activate sensor 805 and collect responses from sensor 805. Such electronics can include a processing unit to analysis signals sensed by sensor 805 and provide measurement results to the surface over standard communication mechanism for operating a well. Alternatively, electronics can include a communications interface to provide signals sensed by sensor 805 to the surface over standard communication mechanism for operating a well, where these sensed signals are analyzed at a processing unit at the surface. Logging cable 874 may be realized as a wireline (multiple power and communication lines), a mono-cable (a single conductor), and/or a slick-line (no conductors for power or communications), or other appropriate structure for use in bore hole 812.

During drilling operations, the drill string 808 can be rotated by the rotary table 807. In addition to, or alternatively, the bottom hole assembly 820 can also be rotated by a motor (e.g., a mud motor) that is located downhole. The drill collars 815 can be used to add weight to the drill bit 826. The drill collars 815 also can stiffen the bottom hole assembly 820 to allow the bottom hole assembly 820 to transfer the added weight to the drill bit 826, and in turn, assist the drill bit 826 in penetrating the surface 804 and subsurface formations 814.

During drilling operations, a mud pump 832 can pump drilling fluid (sometimes known by those of skill in the art as "drilling mud") from a mud pit 834 through a hose 836 into the drill pipe 818 and down to the drill bit 826. The drilling fluid can flow out from the drill bit 826 and be returned to the surface 804 through an annular area 840 between the drill pipe 818 and the sides of the borehole 812. The drilling fluid may then be returned to the mud pit 834, where such fluid is filtered. In some embodiments, the drilling fluid can be used to cool the drill bit 826, as well as to provide lubrication for the drill bit 826 during drilling operations. Additionally, the drilling fluid may be used to remove subsurface formation 814 cuttings created by operating the drill bit 826.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. An apparatus comprising:
a sensor to measure conductivity of a fluid, the sensor having an electric dipole transmitter to induce an electric current in the fluid and having a receiver to detect electric current strength in the fluid in response to inducing the electric current, wherein the electric dipole transmitter has a structure to contain the fluid within the structure or allow flow of the fluid within the structure and includes tapered electrodes being a portion of the structure extending from a body portion of the structure substantially without being in the fluid, the tapered electrodes arranged to receive a voltage applied between the tapered electrodes to induce the electric current.

2. The apparatus of claim 1, wherein the receiver includes a toroid.

3. The apparatus of claim 1, wherein the electric dipole transmitter includes a pair of metal tubes, the metal tubes separated from each other by an insulating tube, such that flow of the fluid can be directed through the metal tubes and the insulating tube.

4. The apparatus of claim 3, wherein the pair of metal tubes includes rigid metal tubes.

5. The apparatus of claim 3, wherein the receiver includes a toroid disposed around the insulating tube.

6. The apparatus of claim 5, wherein each of the metal tubes have a thickness and a groove adjacent the insulating tube such that the toroid is disposed within a groove structure formed by the insulating tube and the grooves of the metal tubes.

7. The apparatus of claim 6, wherein the insulating tube has a center and the toroid has an outer surface at a radial distance from the center of the insulating tube such that the radial distance is less than or equal to an effective radial distance of an outer surface of the metal tubes to the center of the insulating tube.

8. An apparatus comprising:
a sensor to measure conductivity of a fluid, the sensor including:
an electric dipole transmitter to induce an electric current in the fluid, wherein the electric dipole transmitter includes tapered electrodes substantially without being in the fluid, the tapered electrodes arranged to receive a voltage applied between the tapered electrodes to induce the electric current; and
one toroid receiver to detect electric current strength in the fluid.

9. The apparatus of claim 8, further comprising an additional toroid receiver to detect the electric current strength, the additional toroid receiver being wound oppositely to the one toroid receiver.

10. The apparatus of claim 9, wherein the electric dipole transmitter includes:
a first pair of metal tubes, the metal tubes separated from each other by a first insulating tube, such that flow of the fluid can be directed through the first pair of metal tubes and the first insulating tube, each metal tube of the first pair including a tapered electrode of the tapered electrodes; and
a second pair of metal tubes, the metal tubes separated from each other by a second insulating tube, such that flow of the fluid can be directed through the second pair of metal tubes and second insulating tube, each metal tube of the second pair including a tapered electrode of the tapered electrodes.

11. The apparatus of claim 10, wherein one of the metal tubes of the first pair is one of the metal tubes of the second pair.

12. The apparatus of claim 10, wherein each of the metal tubes of the first pair have a thickness and a groove adjacent the first insulating tube such that the one toroid is disposed within a groove structure formed by the first insulating tube and the grooves of the metal tubes of the first pair.

13. The apparatus of claim 9, wherein the apparatus includes a combiner coupled to an output channel from the one toroid receiver and coupled to an output channel from the additional toroid receiver, the combiner arranged relative to the output channels based on a selected signal-to-noise ratio for operation of the sensor.

14. A system comprising:
a sensor to measure conductivity of a fluid, the sensor having an electric dipole transmitter to induce an electric current in the fluid and having a receiver to detect electric current strength in the fluid in response to inducing the electric current, wherein the electric dipole transmitter has a structure to contain the fluid within the structure or allow flow of the fluid within the structure and includes tapered electrodes being a portion of the structure extending from a body portion of the structure substantially without being in the fluid, the tapered electrodes arranged to receive a voltage applied between the tapered electrodes to induce the electric current; and
a processing unit to process a signal from the sensor.

15. The system of claim 14, wherein the system includes a communication line to provide measurement results to the surface of a well when the sensor is downhole in the well.

16. The system of claim 14, wherein the sensor is disposed on a drill collar.

17. The system of claim 14, wherein the sensor includes a voltage source coupled to the electric dipole transmitter, the electric dipole transmitter structured as a pair of metal tubes separated from each other by an insulating tube with each of the metal tubes including a tapered electrode of the tapered electrodes, such that a potential difference can be applied between the metal tubes.

18. The system of claim 14, wherein the sensor includes a voltage source coupled to the electric dipole transmitter, the electric dipole transmitter including a first pair of metal tubes and a second pair of metal tubes, the metal tubes of the first pair separated from each other by a first insulating tube and the metal tubes of the second pair separated from each other by a second insulating tube, the two pairs arranged such that flow of the fluid can be directed through the two pairs of metal tubes.

19. The system of claim 18, wherein the voltage source is coupled to the first pair such that a potential difference can be applied between the metal tubes of the first pair and the voltage source is coupled to the second pair such that a potential difference can be applied between the metal tubes of the second pair, and the receiver unit includes two toroid receivers with one of the toroid receivers disposed around the first insulating tube and the other toroid receiver disposed around the second insulating tube.

20. A method comprising:
measuring conductivity of a fluid using a sensor having an electric dipole transmitter to induce an electric current in the fluid and having a receiver to detect electric current strength in the fluid in response to inducing the electric current, wherein the electric dipole transmitter has a structure to contain the fluid within the structure or allow flow of the fluid within the structure and includes tapered electrodes being a portion of the structure extending from a body portion of the structure substantially without being in the fluid, the tapered electrodes arranged to receive a voltage applied between the tapered electrodes to induce the electric current.

21. The method of claim 20, wherein the method includes:
activating the electric dipole transmitter by applying a potential difference between a pair of metal tubes, the metal tubes separated from each other by an insulating tube, each of the metal tubes including a tapered electrode of the tapered electrodes, the fluid being within the metal tubes and the insulating tube; and
receiving a signal at a toroid receiver with the toroid receiver disposed around the insulating tube.

22. A method comprising:
measuring conductivity of a fluid using a sensor having an electric dipole transmitter to induce an electric current in the fluid and having a receiver to detect electric current strength in the fluid in response to inducing the electric current;
activating the electric dipole transmitter by applying potential differences between two pairs of metal tubes, the activation including:
applying a first potential difference between a first pair of the two pairs, the metal tubes of the first pair separated by a first insulating tube; and
applying a second potential difference between a second pair of the two pairs, the metal tubes of the second pair separated by a second insulating tube, the fluid being within the first and second pairs and within the first and second insulating tubes;
receiving a first signal at a first toroid receiver with the first toroid receiver disposed around the first insulating tube; and
receiving a second signal at a second toroid receiver with the second toroid receiver disposed around the second insulating tube.

23. The method of claim 22, wherein applying potential differences between two pairs of metal tubes includes applying the potential differences with one of the metal tubes of the first pair being one of the metal tubes of the second pair.

24. The method of claim 20, wherein measuring conductivity of a fluid using a sensor includes using a sensor based on a selected signal-to-noise ratio for operation of the sensor.

25. A method comprising:
forming a sensor to measure conductivity of a fluid, including:
disposing an electric dipole transmitter unit to induce an electric current in the fluid, wherein the electric dipole transmitter has a structure to contain the fluid within the structure or allow flow of the fluid within the structure and includes tapered electrodes being a portion of the structure extending from a body portion of the structure substantially without being in the fluid, the tapered electrodes arranged to receive a voltage applied between the tapered electrodes to induce the electric current; and
disposing a receiver unit to detect electric current strength in the fluid in response to inducing the electric current.

26. The method of claim 25, wherein disposing an electric dipole transmitter unit includes disposing a pair of metal tubes with the metal tubes separated from each other by an insulating tube, such that flow of the fluid can be directed through the metal tubes and the insulating tube, and disposing a receiver unit includes disposing a toroid around the insulating tube.

27. The method of claim 26, wherein the method includes disposing each of the metal tubes with a thickness and a groove adjacent the insulating tube such that the toroid is disposed within a groove structure formed by the insulating tube and the grooves of the metal tubes.

28. A method comprising:
forming a sensor to measure conductivity of a fluid, including:
disposing an electric dipole transmitter unit to induce an electric current in the fluid; and
disposing a receiver unit to detect electric current strength in the fluid in response to inducing the electric current, wherein disposing an electric dipole transmitter unit includes disposing two pairs of metal tubes such that the metal tubes of one of the pairs are separated from each other by a first insulating tube and the metal tubes of the other pair are separated from each other by a second insulating tube such that the fluid can be directed into the metal tubes of the two pairs and into the first and second insulating tubes, and disposing a receiver unit includes disposing a first toroid around the first insulating tube and a second toroid around the second insulating tube.

29. The method of claim 28, wherein the method includes disposing the first toroid in a groove formed by the first insulating tube and its corresponding metal tubes.

* * * * *